United States Patent [19]

Lane

[11] Patent Number: 5,733,258
[45] Date of Patent: Mar. 31, 1998

[54] LIVESTOCK BIOLOGICAL AND VACCINE HANDLING SYSTEM TO INCLUDE PISTOL GRIP SYRINGE AND CARTRIDGE

[76] Inventor: Donovan R. Lane, P.O. Box 544, Paso Robles, Calif. 93447

[21] Appl. No.: 532,055

[22] Filed: Sep. 22, 1995

[51] Int. Cl.⁶ .................................................. A61M 31/00
[52] U.S. Cl. ......................... 604/51; 604/209; 604/224; 604/233
[58] Field of Search ............................. 222/309, 939, 222/326, 157; 604/144, 232–234, 209, 211, 223, 224, 222, 136, 61, 51

[56] References Cited

U.S. PATENT DOCUMENTS

| | | | |
|---|---|---|---|
| 2,735,431 | 10/1956 | Swanson | 604/224 X |
| 2,889,085 | 7/1959 | Collins | 222/391 X |
| 3,110,310 | 11/1963 | Cislak | 604/209 X |
| 3,141,583 | 7/1964 | Mapel et al. | 604/234 |
| 3,517,668 | 6/1970 | Brickson | 604/223 X |
| 3,977,401 | 8/1976 | Pike | 604/144 X |
| 4,065,034 | 12/1977 | Callan | 222/391 X |
| 4,472,141 | 9/1984 | Dragan | 604/232 X |
| 4,546,767 | 10/1985 | Smith | 604/224 X |
| 4,594,073 | 6/1986 | Stine | 604/232 X |
| 4,687,472 | 8/1987 | Gross | 604/223 |
| 4,968,303 | 11/1990 | Clarke et al. | |
| 5,112,317 | 5/1992 | Michel | 604/232 X |
| 5,176,657 | 1/1993 | Shields . | |
| 5,318,522 | 6/1994 | D'Antonio . | |

*Primary Examiner*—Mark Bockelman
*Attorney, Agent, or Firm*—Dean P. Edmundson

[57] ABSTRACT

Disclosed is a closed system for the handling of injectable biological products and vaccines used in the treatment and prevention of livestock diseases. This system embodies a prefilled disposable cartridge (44) with disposable needle (48) attached and a metered pistolgrip syringe. The cartridge (44) is breech loaded into the syringe and the product is dispensed from the cartridge by a unique drag link (22) mechanism as a means for advancing the plunger rod (36) and forcing the vaccine from the cartridge (44) into the flesh of animal being treated. Each prefilled cartridge is disposed of after it is emptied and no cleaning is required. A color coding system between the prefilled cartridges 44 and the and the syringe bodies insure that proper dosages are given and that different products are not mixed up or confused with each other by the technicians dispensing the biological products.

12 Claims, 4 Drawing Sheets

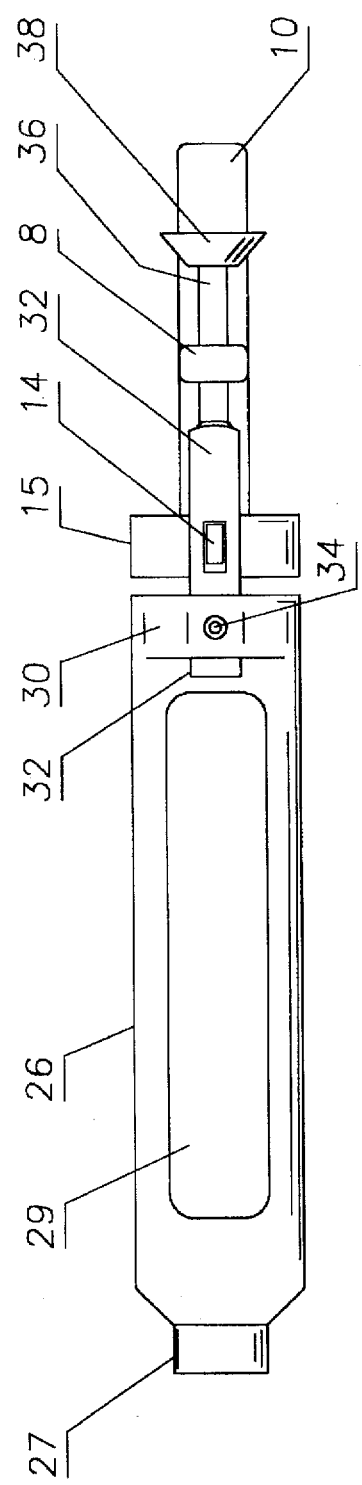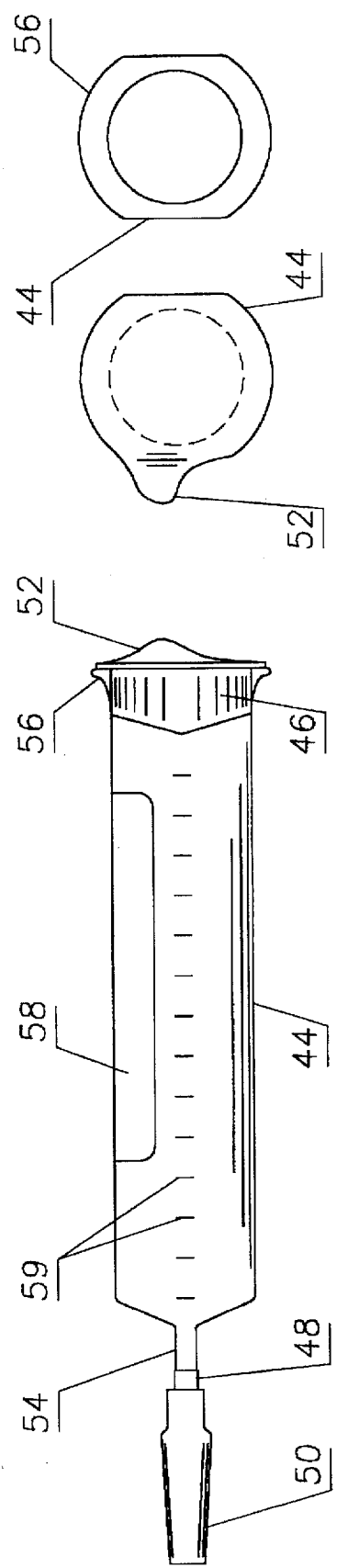

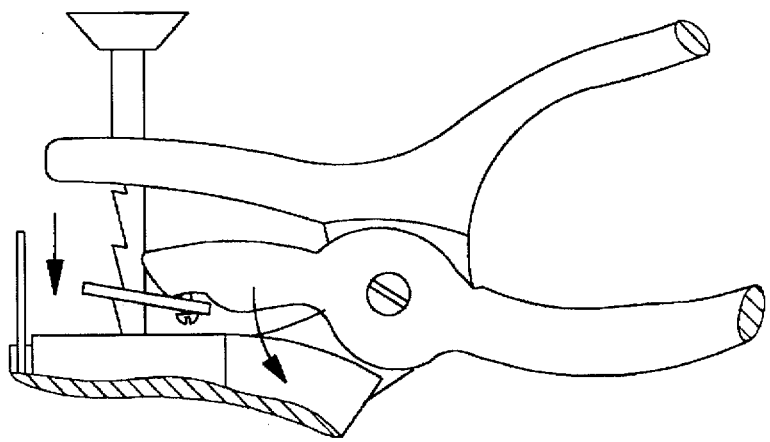
TRIGGER SQUEEZED
FIG. 8
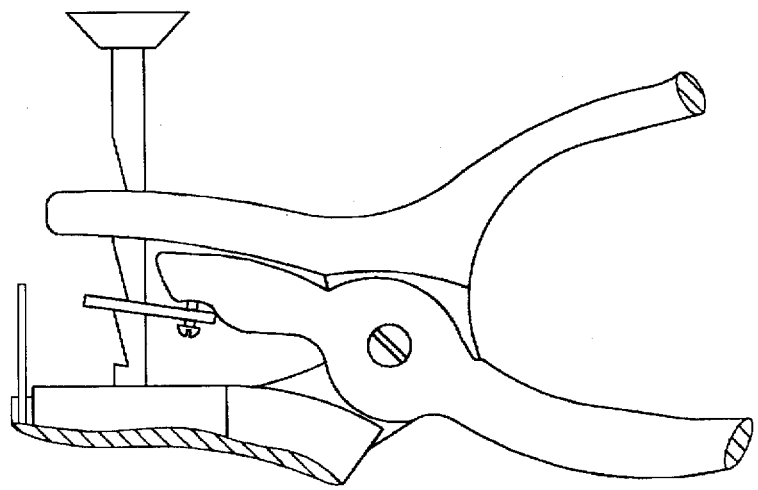
TRIGGER RESTING
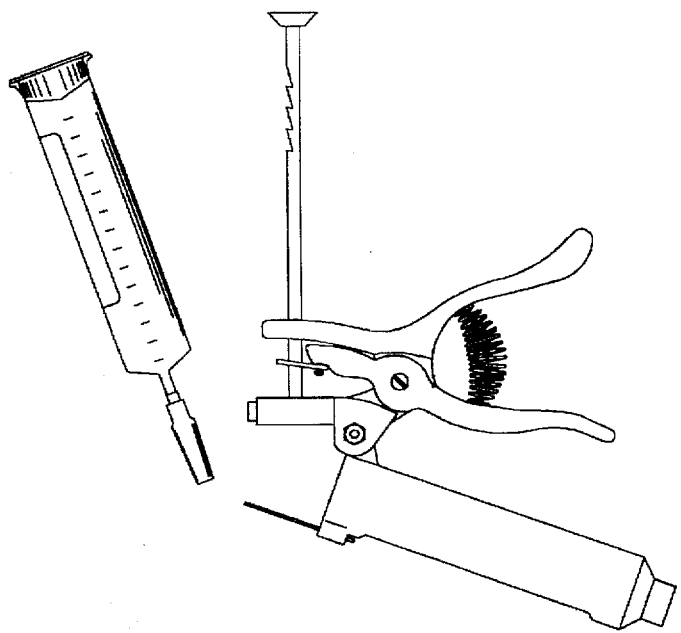
FIG. 6

5,733,258

LIVESTOCK BIOLOGICAL AND VACCINE HANDLING SYSTEM TO INCLUDE PISTOL GRIP SYRINGE AND CARTRIDGE

BACKGROUND

1 Field of Invention

This invention relates to multidose, medical injection syringes used for the vaccination and treatment of livestock diseases. More specifically, the process of a closed handling and delivery system for those injectable biological products used in syringes to include all the steps from the packaging of the product at the pharmaceutical company to the actual injecting of livestock on the farm.

2 Description of Prior Art

Heretofore, multidose, metered, pistol grip type livestock syringes have generally been made from a combination of casted and machined metal parts with glass or plastic barrels sealed on each end with rubber washers. Usually a rubber like plunger is used to force the product from the barrel, through the needle and into the flesh of the animal being injected. This process involves the transferring of the biological product from the package container into the barrel of the syringe allowing for contamination of the product in a multitude of ways. Other numerous disadvantages to these conventional types of livestock syringes and the standard process for the handling of these biologicals are listed below.

(a) The biologicals are packaged at the pharmaceutical companies in glass or plastic containers sealed with a rubber stopper seal, in quantities of usually ten to one hundred doses. At the farm the technician will transfer file biological from the package to the syringe. Sterile medical procedures and expensive sterilization equipment are not common to most farm operations. Consequently the biologicals are easily contaminated by outside air and non-sterile syringe parts, such as the needles used to pierce the rubber seal of the vaccine container, the contaminated syringe barrel, the seals at each end and the plunger of the syringe. Contamination also occurs during the refilling of the syringe as a contaminated needle is pierced through the rubber seal of the standard vaccine bottle and a charge of contaminated air is forced into the bottle to provide backpressure to refill the syringe. The technician may reinsert the needle into the vaccine bottle five to ten times for refilling before the bottle is empty. In addition it is not uncommon to vaccinate 100 or more head of cattle with the stone needle before switching to a clean needle. The more times the vaccine bottle is reentered and the longer the same needle is used, the greater the contamination to the product and the animals being vaccinated. The greater the contamination, the greater the number of cysts and lesions will be found on the carcasses after slaughter. In addition cross contamination causes the rapid spread of many other diseases within the herd.

(b) Slow refilling is another problem as the standard syringe in use today will only give ten or twelve 5 cc doses before it is ready to be refilled. Drawing the high viscosity vaccine into the syringe makes refilling very slow at the working chute.

(c) There are many adjustments on these standard type syringes and many places for them to leak, a constant source of complaints from the technicians. All the rubber gaskets and washers must be in excellent condition and the plunger tension adjusted perfectly to avoid any leakage and even breakage of the syringe barrel.

(d) Most of these pistol grip syringes have a pawl and ratchet type mechanism for advancing the plunger and metering the dosage. If the dosage meter is accidentally set wrong or bumped out of adjustment, a wrong dose will be administered and the mistake may not be detected until after several, maybe many, animals have been given the wrong dose. Also as the teeth on these ratchets wear down and as the springs become weaker they will occasionally skip a notch thereby administering a "short dose" now and then. It is difficult to detect the difference between a four milliliter dose and a five milliliter dose, based on the feel of the trigger.

(e) In general, these metal and glass syringes are relatively expensive. They have a multitude of replaceable parts which are not interchangeable between the different brands of syringes. It therefore becomes difficult to find a farm supply store with an adequate inventory of parts for all guns.

(f) If the metal syringe is equipped with a glass barrel, it can easily be broken causing the loss of expensive product and time. If it is equipped with a plastic barrel it may become out of round and begin to leak.

(g) When several different vaccines and biological products are being used, mix ups often occur. The mix ups usually occur during the refilling process when several technicians are working in the same area giving a series of injections to animals as they come through the working chute. The syringes all look the same and many of the biological products are similar in color and consistency. Consequently it is not uncommon for the wrong product to be loaded into the wrong syringe.

Prefilled cartridges heretofore, have generally been utilized in single dose human applications and occasionally have been tried for livestock, again mostly as single dose ampoules or cartridges. The ampoule may have a pierceable membrane, to be perforated by a needle that is sharpened on both ends and fixed to the syringe body, not the cartridge. This was the method used in the U.S. Pat. No. 2,778,359 to Freidman (1957) and several other syringes, mainly designed for human use, that have followed. Multidose, metered, pistolgrip syringes became popular for livestock use during the 1960's and the basic state of the art is best characterized in the U.S. Pat. No. 3,110,310 to Cislak (1961). To fill this syringe the needle of the syringe is pierced through the rubber seal of the vaccine bottle and a charge of air is pushed into the bottle to supply the needed backpressure. The vaccine or biological product is then drawn from the original package or bottle into the syringe by pulling rearward on the plunger rod. The biological is dispensed when the trigger is squeezed and a pawl attached to the trigger mechanism pushes against a notch on the plunger rod to advance the plunger rod. Generally each notch on the plunger rod represents one milliliter of biological product dispensed and the syringes are adjustable between one and five milliliters. Relatively few significant improvements or modifications have been made in this standard type of pistol grip syringe over the past 35 years.

A marriage between a metered, multidose, pistol grip syringe and a prefilled cartridge was attempted in U.S. Pat. No. 3,517,668 to Brickson (1970). A pierceable cartridge and a needle sharpened on both ends was used, preventing the system from being classified as a completely closed system, since the needle is fixed to the syringe and could likely be used to pierce more than one cartridge therefore contaminating all the cartridges following the first one used. In addition a half used cartridge cannot be stored and later reused and maintain its closed system status because the seal has been pierced and the cartridge is not married to the needle with which it was first used. The mechanism of the trigger and plunger rod advance system are somewhat complicated and are not skip proof because the springs will weaken and the pawls and ratchet notches will wear down with use. This appears to be a rather slow loading syringe because the barrel must be unscrewed, the cartridge loaded into the barrel and the barrel screwed back onto the syringe body. U.S. Pat. No. 4,368,731 to Schramm (1983) utilizes a glass ampoule with a permanently affixed needle. If that needle is bent or broken the ampoule is no longer usable. This syringe also requires unscrewing and screwing the barrel to lead the ampoule.

The syringe with the closest relationship to my invention is U.S. Pat. No. 4,738,664 to Prindle (1988). This syringe is similar to the Cislak syringe but has been adapted to hold a modified disposable syringe which is bayonet mounted onto the front of the original pistol grip mechanism. The use of a prefilled cartridge is not indicated for this syringe. The vaccine must still be drawn from rise bottle into the syringe. The advantage over the original Cislak is that no cleaning is necessary, the syringe barrel is disposed of alter the vaccinations are completed. It is not a closed system. In addition the mounting of the disposable syringe is somewhat cumbersome, in that the disposable syringe must first be twist lock connected to the pistol grip mechanism and then the plunger rod is twist lock coupled to the plunger. Finally, a support is wedged onto the end of the disposable syringe but no real support is provided for the full length of the apparatus. U.S. Pat. No. 4,968,303 to Clarke et al (1990) is a pistol grip syringe specifically designed to handle single dose cartridges for a specific product. One injection is made and the cartridge is discarded and a new one loaded for the next animal to be injected. There is no plunger brake and when the squeeze pressure on the trigger and handle is released the plunger rod is retracted to its' original position. The needle is permanently fixed to the cartridge as in the Schramm syringe, so that it is not replaceable if bent or broken.

OBJECTS AND ADVANTAGES

This invention combines a unique cartridge package for vaccines and other injectable biologicals with an innovative new pistol grip syringe to form an entirely new closed system concept or process in the handling of injectables for use in livestock. At the pharmaceutical company, the biological product will be packaged in the sterile cartridges. The cartridge will be sealed on the anterior or nipple end with a removable, disposable needle of the proper gage and length as required for the product being used and the class of livestock being treated. The posterior end of this cylindrical cartridge will be primarily sealed by the insertion of a pliable rubber-like plunger. In addition a color coded tear away foil seal will be glued to the flat flange on the extreme posterior end of the cartridge. The cartridge will be labeled with a colored label matched to the colored foil seal which will in turn indicate the color of the syringe to be used with that cartridge. At the farm supply store the customer will be sold or given the proper colored syringe to match the color of the label and seal office biological product that he/she has purchased. That specific colored syringe has been pre-metered to dispense only the precise dosage recommended for the product with the matching colored label. If the label of the product is green, the syringe will be green. If the required dosage for the green packaged product is 5 milliliters, the green syringes will be metered to dispense precisely 5 milliliters per squeeze of the trigger. There will be no adjustments for dosage size on these syringes. The dosage for another product may be 2 milliliters and the product may have a yellow label. The syringe distributed with that product will be yellow and will dispense only 2 milliliters of product per squeeze. The technician at the farm will tear away the foil seal and lead the cartridge into the syringe, just as shells are loaded into a breech loading shotgun. The sheath protector will be removed from the needle and the vaccinating will begin. Thus, the biological product has remained completely within a closed system from the time it was sealed under sterile conditions at the manufacturer until the sheath was removed from the needle on the farm.

(a) The combination of this entire process and the mechanical aspects of the designed cartridges and syringes will insure that the original sterile condition of the product will be maintained from the manufacturer until the product is injected into the livestock. All chance of contamination, either mechanical or airborne, as was described in part (a) under BACKGROUND and PRIOR ART (above), has been eliminated because the product has been contained within this closed system from packaging until injection. With a sterile needle attached to each new cartridge, the livestock manager can be assumed, that at least, the needle is being changed every time a new cartridge is loaded. Some management procedures require that the needles be changed even more frequently. If this is the case, the supplied needle may be removed at any interval and be replaced with a standard, over the counter disposable needle. Interchangeability of needles is also necessary to accommodate replacement of broken, bent or dulled needles. The needles supplied with the prefilled cartridges will conform to the recommendations of the manufacturer for that particular application for which they are intended. For example if the vaccine is to be administered intramuscularly to cattle, the cartridge may come supplied with a one inch, 16 gage needle. If the vaccine is a subcutaneous injection for mature sows, the cartridge may have a ⅝ inch, 14 gage needle attached. This cleaner, more sterile process of injecting livestock will produce an immediate drop in injection site lesions and cysts.

(b) Reloading will be rapid and simple. When the cartridge has been spent, the syringe will be opened, just as a breech loaded shotgun is broken open. The spent cartridge and attached needle are discarded into the trash and a new prefilled cartridge with attached sterile needle is loaded into the syringe. The syringe is then snapped closed, the sheath removed from the needle and the syringe is again ready for use. A unique closure latch secures the syringe barrel in the closed position.

(c) There will be no leakage with this syringe because all the mechanical and adjustable parts that come in direct contact with the biological product, and are usually the source of leaks in the current state of the art syringes, have been eliminated and replaced by disposable cartridges with their own plungers which are obviously replaced with each cartridge change.

(d) The mechanism that forces the plunger rod forward in this invention is a hinged drag link and has absolutely no adjustment. Because of the angle and the travel radius of the trigger arm, the drag link makes contact with a small notch on the top of the plunger rod and pulls slightly down and forward on file plunger rod. In addition the top and bottom edges of the rectangular hole in the drag link, bind on the plunger rod making skips virtually non existent. The drag link is not reliant upon a small delicate spring to hold it in the notch as is the case with the ratchet and pawl mechanisms used in the standard state of the art syringes on the market today. A 5 milliliter syringe can only dispense 5 milliliters, no more, no less. There is no need to adjust because the syringes are specific to the product with which they are sold. When a product with a recommended 5 milliliter dosage is sold, it comes with a 5 milliliter dispensing syringe. In almost all vaccines the dosages are constant without regard to the weight or even the species of the animal to be vaccinated. Without an adjustment the syringe will always give the proper dose. If the syringe malfunctions, no dose will be given and this will be detected by the technician immediately.

(e) These syringes will be primarily made from hard plastics through the injection mold process and will be relatively inexpensive compared to the machined metal syringes on the market today. As is shown in the design, they are a very simple mechanism and consequently very light weight and easy to handle. Manufacturers may elect to give the syringes to the buyers of larger quantities of the biological products. Because these syringes will be made from durable hard plastic and hardened metal parts, their wear life will be comparable to the all metal syringes. However if they should break or fail in some way, they will be inexpensive enough to replace rather than repair.

(f) With no glass in the construction of this syringe, the problems of product loss and work slowdowns to replace the broken glass barrels are eliminated.

(g) Mistakenly switching the vaccines in the working area is very common and the wrong vaccines may be inadvertently refilled into the syringes. This happens because the color and consistency of many of the vaccines are very similar and are even packaged in similar appearing containers. With this unique color coded system or process, the technician is not even required to be able to read the label to get the proper product into his syringe. All he or she must know is that the yellow cartridges go in the yellow syringe, the blue cartridges in the blue syringe and so on. The technician won't even need to adjust the dosage level or fine tension on file plunger. He can't because there are no adjustments.

(h) With all of the above mentioned advantages to this system, the one most popular with the farmers and ranchers will be that no cleaning of the syringes is necessary, yet absolutely sterile conditions will be maintained.

Further objects and advantages of this new process and accompanying syringe and cartridges will become apparent from consideration of the ensuing drawings and description.

DRAWING FIGURES

FIG. 2 is the top view of the stone syringe.

FIG. 3 is the side view of the prefilled cartridge with the sheathed disposable needle attached and the foil seal glued on.

FIG. 4 is the rear view of the cartridge with the foil seal in place.

FIG. 5 is the rear view of the cartridge with the foil seal removed.

FIG. 6 demonstrates the loading of the cartridge into the syringe.

Figure 1:
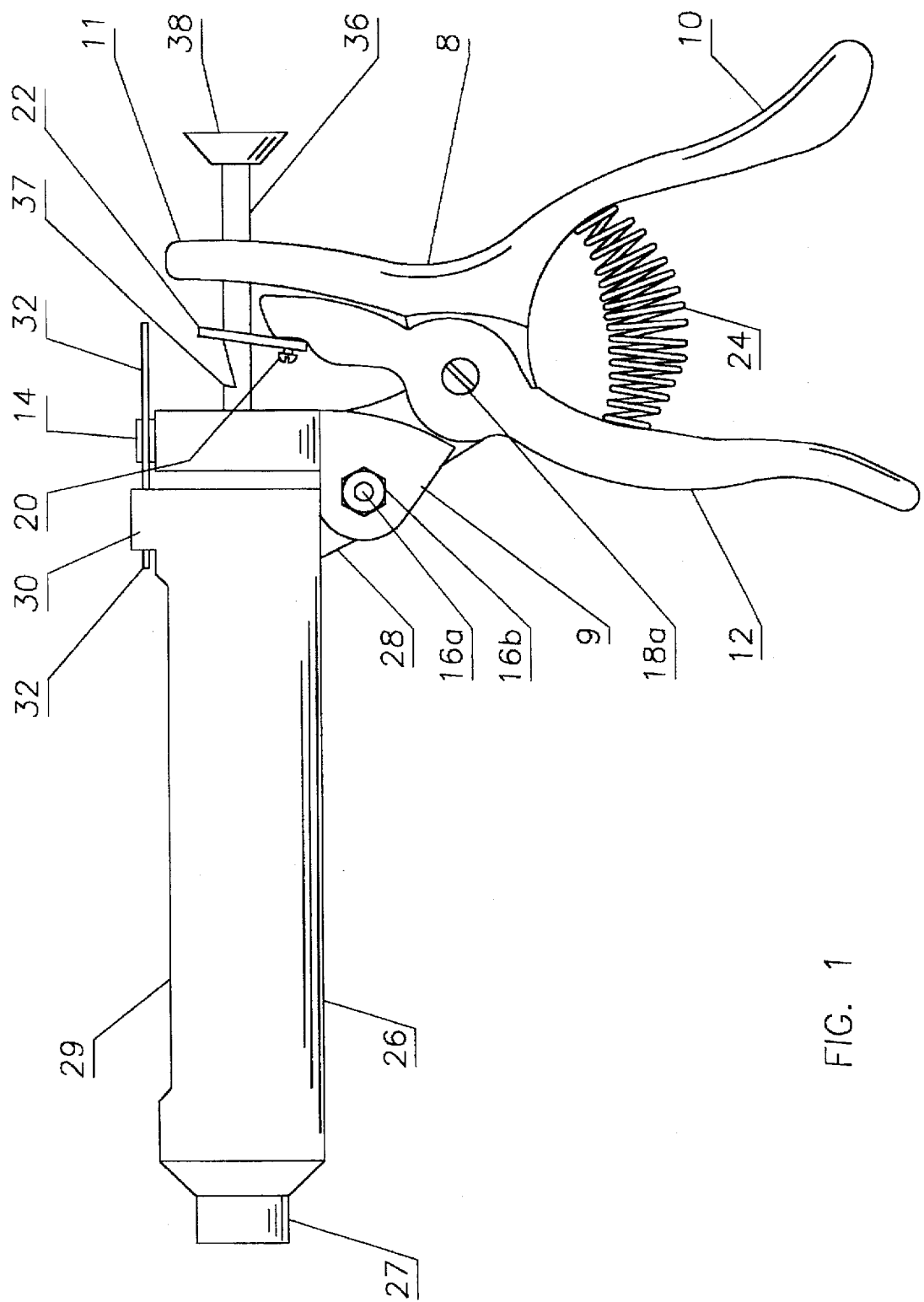
FIG. 1 is the side view of the pistol grip syringe with no cartridge loaded.
Figure 7:
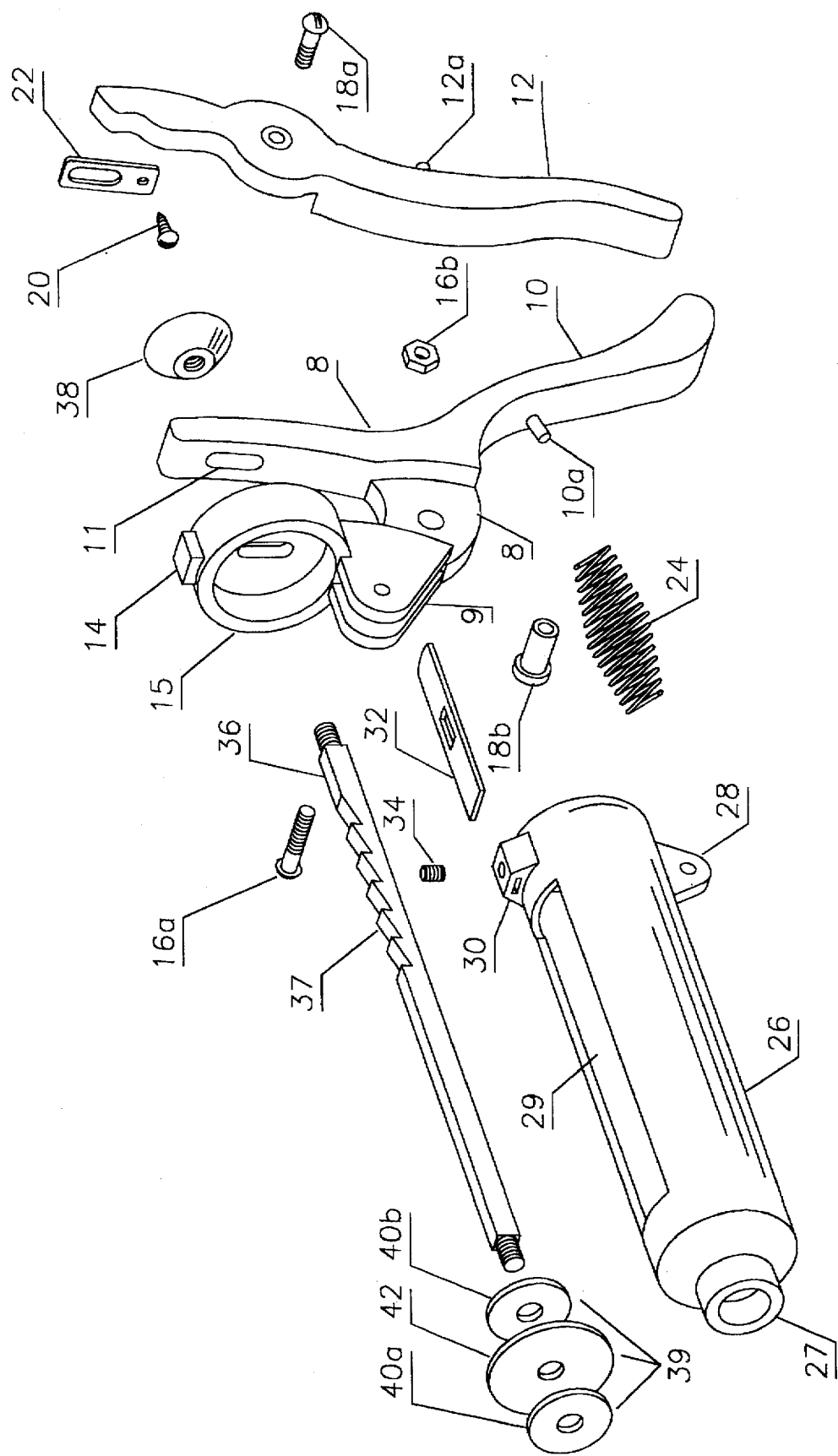

FIG. 7 is a ¾ exploded view of the syringe.

FIG. 8 demonstrates the motion of the trigger, drag link and plunger rod mechanism

| Reference Numerals in Drawings | | | |
|---|---|---|---|
| 8 | main frame | 29 | observation window |
| 9 | loading pivot base | 30 | closure latch mounting bracket |
| 10 | frame handle | 32 | closure latch |
| 10a | spring peg | 34 | set screw |
| 11 | plunger rod guide | 36 | plunger rod |
| 12 | trigger | 37 | dosage metering notch |
| 12a | spring peg | 38 | plunger rod handle |
| 14 | closure latch receiver | 39 | piston brake assembly |
| 15 | recessed plunger back plate | 40a | threaded flat washer |
| 16a | loading pivot screw | 40b | threaded flat washer |
| 16b | nut to loading pivot screw | 42 | piston brake (pliable rubber like) |
| 18a | trigger pivot sleeve screw | 44 | prefilled disposable cartridge |
| 18b | threaded sleeve | 46 | plunger (pliable rubber like) |
| 20 | wood screw | 48 | disposable needle |
| 22 | drag link | 50 | needle sheath |
| 24 | compression spring | 52 | colored foil seal |
| 26 | barrel | 54 | cartridge nipple |
| 27 | needle protector collar | 56 | cartridge flange |
| 28 | loading pivot | 58 | colored label |
| | | 59 | dosage indication marks |

DESCRIPTION OF FIGS. 1 to 8

The essence of this invention combines the mechanical aspects of the items in FIGS. 1 through 8 to create a process which I term, a closed delivery system for the administration of the most common injectable vaccines and biological products used in the treatment and prevention of diseases and ailments in livestock. The goals set forth in this process are as follows:

(a) Create maximum sterile conditions and eliminate any chance of outside elements contaminating the biological product. This is done through a closed delivery system where the product is packaged and sealed under absolutely sterile conditions at the pharmaceutical manufacturer and remains sealed until the animal is actually injected with the product.

(b) Insure that the proper sized needle is used in the vaccination process and that clean sterile needles are rotated on a regular basis.

(c) Create a system that is economically competitive with the current state of the art practices and is faster and simpler to use than the methods we are using today.

(d) Create a system or process where the technicians on the livestock processing crews can load and reload their syringes rapidly without the chance of mixing up the products or the syringes, especially between the workers on the crew.

This process or closed delivery system, encompasses four basic elements to accomplish the goals listed above.

(1) The packaging of the product in sealed, sterile, disposable cartridges 44, as is illustrated in FIGS. 3, 4 and 5.

(2) The color coding system between the cartridges and the syringes.

(3) The correct sized needle 48 packaged with the product and the assurance that a clean, flesh needle 48 will be used at least every time the cartridge 44 is emptied and changed.

(4) The light weight, quick loading and inexpensive syringe illustrated in FIGS. 1, 2, 6 and 7, designed to accommodate the above cartridges 44.

A typical embodiment of the syringe is illustrated in FIGS. 1, 2, 6, 7 and 8 and detail of the disposable cartridge is illustrated in FIGS. 3, 4 and 5. These are the two basic mechanical elements of the invention and combine to form a process or closed system designed to simplify, cheapen and improve the sterile nature of injectable biological products used in the prevention and treatment of livestock diseases. The cartridge 44 is a cylindrical, hollow tube made of an unbreakable clear plastic like substance. The anterior end of the cartridge 44 is necked down to a nipple 54, sized to accommodate a disposable injection needle 48 of the proper gage and length as recommended by the manufacturer to suit the use of the product packaged in the cartridge 44 and the class of livestock to which the product is intended to be administered. The needle 48 is covered and sealed with a protective sheath 50. The combination of the needle 48 and the sheath 50 create the seal on the anterior end of the cartridge 44. The cartridge 44 is formed into a flat flange 56 on the posterior end, perpendicular to the tube of the cartridge 44. The product is sealed in the cartridge 44, on this flanged posterior end by the insertion of a pliable rubber like plunger 46. Each loaded cartridge 44 is labeled with a specific colored label 58 and secondarily sealed on the flanged end with a glued on, tear away foil seal 52 also colored to match the label 58. Each separate biological product will have its own unique color which will be used for the label 58, the tear away foil seal 52 and the syringe body itself. The cartridge 44 is marked with the proper dosage increments 59, which can be viewed through the observation window 29 of the syringe body to give the technician an indication of how many doses have been used and how many doses remain in the cartridge 44.

The exploded view of FIG. 7 shows detail of the parts of the pistol grip syringe body. The main frame 8, barrel 26, trigger 12 and plunger rod handle 38 are made from a hard injection molded plastic. The barrel 26 is cylindrical in shape with an inside diameter of the proper dimension so that the cartridge 44 will slide into the barrel 26 with a fairly snug fit. On the anterior end of the barrel 26 is a thickened needle protector collar 27 with an inside diameter of sufficient size to allow the disposable needle 48 and the needle sheath 50 to pass through easily when the prefilled cartridge 44 is loaded into the syringe body. An observation window 29 is cut longitudinally in the top of the barrel 26 as a means for the technician to observe the movement of the plunger 46 as it advances through the cartridge 44 and to read the dosage indication marks 59 inscribed on the cartridge 44. The closure latch mounting bracket 30 is molded onto the top, posterior end of the barrel 26. A slot is cut through the bracket 30, parallel to and lying flat on top of the barrel 26 to receive the closure latch 32. A hole is drilled and tapped through file top of the mounting bracket 30 to accommodate the set screw 34 as a means seeming the closure latch 32 in place. A loading pivot 28 is molded to the posterior bottom end of the barrel 26 with a hole as a means for mounting the barrel 26 to the main frame 8 and to pivot axially on the loading pivot screw 16a as a means for breech loading and unloading cartridges 44 into the barrel 26 of the syringe. The loading pivot screw 16a is secured in place with the loading pivot nut 16b. The closure latch 32 is made from flat spring steel with a punched rectangular hole sized slightly larger than the closure latch receiver 14. The main frame 8 and the trigger 12 are mounted together with the trigger pivot sleeve screw 18a and the threaded sleeve 18b and pivot on each other in a scissor like fashion. The compression spring 24 is mounted between the trigger 12 and the main frame handle 10 and held in place by the spring pegs 10a and 12a. The barrel 26 is mounted to the main frame 8 by sliding the loading pivot 28 between the forks of the loading pivot base 9 and securing with the loading pivot screw 16a and nut 16b. The plunger back plate 15 is round in shape and molded with an ample inside diameter and recessed dimensions so as to contain the entire plunger brake assembly 39 when the plunger rod 36 is retracted to its extreme rearward position. There is a slot in the plunger back plate 15 and the plunger rod guide 11 as a means to guide the travel of the flattened plunger rod 36. The closure latch receiver 14 is a raised rectangular shape, molded to the top of the plunger back plate 15 and made just slightly smaller than the rectangular hole, punched in the closure latch 32. This allows the closure latch 32 to snap over the closure latch receiver 14 when the syringe is loaded axed closed and will hold the barrel 26 in that closed position. The plunger rod 36 is flattened its entire length except for the extreme anterior end where it is round and threaded to accommodate the piston brake assembly 39. The plunger rod 36 is notched 37 along its topside as a means to calibrate and dispense metered doses. When the trigger is squeezed, the plunger rod 36 travels the precise distance to push the plunger 46 into the cartridge 44 to dispense the proper dosage. The plunger rod 36 is also threaded on the flattened posterior end so that the plunger rod handle 38 may be screwed on to the plunger rod 36. The piston brake assembly consists of two metal threaded flat washers 40a and 40b and a pliable rubber like flat washer or piston brake 42. The two metal washers 40a and 40b are screwed onto the round, threaded anterior end of the plunger rod 36 with the pliable piston brake 42 between them. The drag link 22 is made from hardened flat steel with a round hole to accommodate a wood screw 20 for attaching it to the trigger and a rectangular hole of sufficient size to allow the flattened plunger rod 36 to pass through. All of the plastic outputs of the syringe including the main frame 8, the trigger 12, the barrel 26 and the plunger rod handle 38 will be colored the same as the color of the label 58 and the tear away foil seal 52 on the cartridges 44 sold with that syringe. The dosage metering notches 37 on the plunger rod 36 will be calibrated to give the dosage recommended on the colored label.

Operation of FIGS. 1 to 7

The combination of the process or method of this invention and the operation of the syringe utilizing the cartridge begins at the pharmaceutical manufacturer. The injectable biological product is packaged in the cartridge 44 and sealed on the anterior end by the disposable needle 48 and its sheath 50. The posterior end is sealed by the plunger 46 and the color coded, tear away, foil seal 52. A colored label 58 is glued to the cartridge 44. A corresponding color coded pistol grip syringe is distributed by the pharmaceutical manufacturer in conjunction with the prefilled cartridge. The manner of using the prefilled cartridge 44 in combination with the syringe begins by removing the colored tear away foil seal 52 from the posterior end of the prefilled cartridge 44. While grasping the syringe in a normal pistol grip fashion with the right hand, the technician pulls the plunger rod handle 38 with the left hand until the plunger rod 36 is in the extreme rearward position. With the right thumb, the closure latch 32 is pushed slightly upward while applying downward pressure to the anterior top side of the barrel 26. The barrel 26 and main frame 8 will rotate axially on the loading pivot screw 16a, breaking open the syringe into the loading position as is illustrated in FIG. 6. The cartridge 44 is loaded into the barrel 26 of the syringe just as shotgun shells are breech loaded into a shotgun. Care is taken to insure that the cartridge 44 is loaded with the dosage indication marks 59 facing up so that they may be seen through the observation window 29. The barrel 26 is then rotated upward to its original closed position. As the barrel 26 approaches its final closed position the flat spring steel closure latch 32 rides up on the closure latch receiver 14 until the rectangular hole in the latch 32 snaps over the receiver 14 and secures the syringe in the closed position. The sheath 50 is removed from the needle 48 and the syringe is ready for use. To dispense the biological product the technician squeezes the trigger 12 and the handle 10 which rotate axially on the trigger pivot sleeve 18b and screw 18a. The compression spring 24 is compressed as the trigger is squeezed. As the trigger 12 is squeezed the top portion of the trigger 12 moves in an arc pattern, forward and downward in relation to the plunger rod 36. This motion as is illustrated in FIG. 8, pulls the drag link 22 forward while maintaining downward pressure on the plunger rod 36. In addition a binding action is created from both the top and bottom edges of the slot in the drag link 22 against the plunger rod 36. That downward pressure and binding action holds the drag link 22 securely in the dosage motoring notch 37 on the plunger rod 36 which in turn pulls or advances the plunger rod 36 forward. The piston brake assembly 39, mounted on the extreme anterior end of the plunger rod 36 pushes the pliable rubber-like plunger 46 forward in the cartridge 44 forcing the biological product through the nipple 54 and the needle 48 dispensing the product into the flesh of the animal being treated. When the trigger is released the compression spring 24 forces the trigger 12 and the handle 10 apart reversing their original rotation. The drag link 22 is lifted up and pushed rearward along the plunger rod 36 where it drops into the next dosage metering notch 37, ready to dispense the next dose. The snug fitting plunger brake assembly 39 holds the plunger rod 36 in its forward position so that it does not retract when the trigger is released. As the doses are dispensed, the technician may observe the position of the plunger 46 through the observation window 29. When the cartridge 44 is emptied the plunger rod 36 is retracted to its extreme rearward position by pulling back on the plunger rod handle 38. The syringe is broke open, as was detailed earlier, into the loading or unloading position and the cartridge 44 and needle 48 are removed and discarded.

Summary, Ramifications and Scope

Accordingly the reader will see that the process for handling vaccines and other injectable biologicals for livestock is dramatically improved through the use of this invention. The advantages listed below become apparent as the reader begins to visualize how the product is handled today and how that will change when the process utilizing the prefilled disposable cartridge and the described pistol-grip syringe body is implemented.

Sanitary and sterile conditions are virtually guaranteed by the use of this invention. The product never makes any physical contact with any parts of the syringe. The product is fully contained within the closed system of the cartridge and the attached disposable needle. A clean sterile needle is attached to each prefilled cartridge, therefore insuring that a new, sterile needle will be used each time a cartridge is emptied and a new, full cartridge is loaded.

No clean up of the syringes is necessary.

Rapid refilling is as quick and as easy as removing the spent cartridge and sliding a new one into the syringe.

There are no leaks and no waste of expensive product with this system.

Skips are more easily detectable because a skip will mean the trigger did not advance and no dosage was given. It will be impossible to give a partial dose.

Made from a hard plastic material through the injection mold process, the cost of this syringe will be considerably lower as compared to the typical metal syringes which require extensive machining.

Mix ups in the work area will be greatly reduced because the labels of the cartridges will be color coded to match the syringes with which they are to be used.

Although some example specifications are implied throughout the text of the above descriptions, these should not be construed as limiting the scope of the invention but as merely providing illustrations so that the reader may better visualize the embodiment of the invention. The size of both cartridges and syringes may be varied to fit specific consumer needs within the industry. This specific closed delivery system for injectable biologicals will work well for the treatment and vaccinations of all classes of livestock including beef cattle, dairy cattle, swine, sheep, goats, horses and poultry.

With a few structural changes but utilizing the same mechanical principles described in the above invention, the syringe may be modified to be used with the standard disposable syringes on the market today. As an example the technician would attach a disposable needle to a standard disposable syringe. The vaccine would be drawn into the syringe from the standard container used today and the filled disposable syringe loaded into the modified pistol grip gun or syringe. The advantages to this system over the current system in use today are:

Vastly improved sterile conditions.

No cleaning of used syringes.

No leaking gaskets or plungers.

Less expensive syringe bodies.

A sterile method of handling modified live viruses that require mixing.

Thus the scope of the invention should be determined by the appended claims and their legal equivalents, rather than by the examples given.

I claim:

1. An injecting device for handling and injecting a biological product for livestock comprising:

(a) a prefilled disposable cartridge containing sterile biological product; wherein said cartridge includes anterior and posterior ends and a plunger positioned in said posterior end; wherein said plunger is movable in said cartridge to dispense said biological product through said anterior end;

(b) pistol grip syringe body dispensing a member including a main frame and further comprising:

(i) a tubular barrel portion sized for receiving and supporting said cartridge; wherein said barrel portion is hinged to said main frame and is pivotable thereon between open and closed positions; wherein said cartridge is slidably inserted into or removed from said barrel portion when said barrel portion is in said open position;

(ii) a trigger movably mounted on said frame and having an upper end;

(iii) a link carried by said upper end of said trigger and including an aperture therethrough;

(iv) an elongated plunger rod having a forward end; wherein said plunger rod extends through said aperture in said link and is axially aligned with said cartridge;

wherein said link is mounted such that movement of said upper end of said trigger toward said cartridge when positioned in said barrel portion causes said link to engage said plunger rod and thereby move said plunger rod against said plunger in said cartridge; and wherein rearward movement of said upper end of said trigger causes said link to move rearwardly with respect to said plunger rod.

2. An injecting device in accordance with claim 1, further comprising a color coding system wherein said cartridge and said dispensing means each include the same color identification.

3. An injecting device in accordance with claim 1, further comprising a needle detachably secured to said anterior end of said cartridge.

4. An injecting device in accordance with claim 1, wherein said trigger is pivotally mounted on said dispensing means and is movable between open and retracted positions; wherein movement of said trigger from said open to said retracted position causes said plunger rod to move against said plunger to thereby dispense one dose of said biological product from said cartridge.

5. An injecting device in accordance with claim 1, further comprising brake means on said forward end of said plunger rod.

6. An injecting device in accordance with claim 1, wherein said barrel portion has a posterior end which is pivotally mounted on said dispensing means; and wherein said posterior end of said cartridge is sealed with a color-coded foil seal.

7. A closed delivery system for handling and injecting a biological product for livestock comprising:

(a) a prefilled disposable cartridge containing sterile biological product; wherein said cartridge includes anterior and posterior ends and a plunger positioned in said posterior end; wherein said plunger is movable in said cartridge to dispense said biological product through said anterior end;

(b) pistol grip syringe body dispensing a member including a main frame and further comprising:

(i) a tubular barrel portion sized for receiving and supporting said cartridge; wherein said barrel portion is hinged to said main frame and is pivotable thereon between open and closed positions; wherein said cartridge is slidably inserted into or removed from said barrel portion when said barrel portion is in said open position;

(ii) a trigger movably mounted on said frame and having an upper end;

(iii) a link carried by said upper end of said trigger and including an aperture therethrough;

(iv) an elongated plunger rod having a forward end; wherein said plunger rod extends through said aperture in said link and is axially aligned with said cartridge;

wherein said link is mounted such that movement of said upper end of said trigger toward said cartridge when positioned in said barrel portion causes said link to engage said plunger rod and thereby move said plunger rod against said plunger in said cartridge; and wherein rearward movement of said upper end of said trigger causes said link to move rearwardly with respect to said plunger rod.

8. A closed delivery system in accordance with claim 7, further comprising a color coding system wherein said cartridge and said dispensing means each include the same color identification.

9. A closed delivery system in accordance with claim 7, further comprising a needle detachably secured to said anterior end of said cartridge.

10. A closed delivery system in accordance with claim 7, wherein said trigger is pivotally mounted on said dispensing means and is movable between open and retracted positions; wherein movement of said trigger from said open to said retracted position causes said plunger rod to move against said plunger to thereby dispense one dose of said biological product from said cartridge.

11. A method for delivering a sterile biological product to livestock comprising the steps of:

(a) providing a disposable cartridge having anterior and posterior ends and an internal cavity; wherein said cavity contains said sterile biological product; wherein said posterior end of said cartridge is closed with a plunger and is sealed;

(b) providing a pistol grip syringe body dispensing member comprising:

(i) a main frame;

(ii) a tubular barrel portion sized for receiving and supporting said cartridge; wherein said barrel portion is hinged to said main frame and is pivotal thereon between open and closed positions; wherein said cartridge is slidably inserted into or removed from said barrel portion when said barrel portion is in said open position;

(iii) a trigger movably mounted on said main frame and having an upper end;

(iv) a link carried by said upper end of said trigger and including an aperture therethrough;

(v) an elongated plunger rod having a forward end; wherein said plunger rod extends through said aperture in said link and is axially aligned with said cartridge;

wherein said link is mounted such that movement of said upper end of said trigger toward said cartridge when positioned in said barrel portion causes said link to engage said plunger rod and thereby move said plunger rod against said plunger in said cartridge; and wherein rearward movement of said upper end of said trigger causes said link to move rearwardly with respect to said plunger rod;

(c) unsealing said cartridge and inserting said cartridge into said barrel portion of said dispensing means;

(d) attaching a needle to said anterior end of said cartridge;

(e) inserting said needle into the flesh of an animal; and (f) moving said trigger in a manner such that said upper end thereof causes said plunger rod to move forwardly against said plunger to thereby dispense biological product from said cartridge into said animal.

12. A method in accordance with claim 11, further comprising the step of marking said cartridge and said dispensing means with the same color.

* * * * *